(12) United States Patent
Nakai et al.

(10) Patent No.: US 10,008,426 B2
(45) Date of Patent: Jun. 26, 2018

(54) ETCHING METHOD AND ETCHANT

(71) Applicant: TOSHIBA MEMORY CORPORATION, Minato-ku, Tokyo (JP)

(72) Inventors: Takehiro Nakai, Mie (JP); Norihiko Tsuchiya, Kanagawa (JP); Sakae Funo, Tokyo (JP); Junichi Shimada, Tokyo (JP); Youko Itabashi, Tokyo (JP)

(73) Assignee: TOSHIBA MEMORY CORPORATION, Tokyo (JP)

( * ) Notice: Subject to any disclaimer, the term of this patent is extended or adjusted under 35 U.S.C. 154(b) by 0 days. days.

(21) Appl. No.: 15/254,310

(22) Filed: Sep. 1, 2016

(65) Prior Publication Data
US 2017/0154829 A1   Jun. 1, 2017

(30) Foreign Application Priority Data
Nov. 27, 2015   (JP) .................. 2015-232057

(51) Int. Cl.
| H01L 21/66 | (2006.01) |
| H01L 21/306 | (2006.01) |
| H01L 21/02 | (2006.01) |
| C09K 13/08 | (2006.01) |
| H01L 21/30 | (2006.01) |

(52) U.S. Cl.
CPC .............. H01L 22/24 (2013.01); C09K 13/08 (2013.01); H01L 21/02238 (2013.01); H01L 21/30604 (2013.01)

(58) Field of Classification Search
None
See application file for complete search history.

(56) References Cited

U.S. PATENT DOCUMENTS

| 4,787,997 | A | 11/1988 | Saito et al. | |
| 5,635,463 | A * | 6/1997 | Muraoka | C11D 1/004 252/79.3 |
| 6,066,571 | A * | 5/2000 | Usuda | H01L 21/02052 257/E21.228 |
| 7,811,464 | B2 | 10/2010 | Kume | |
| 2004/0137752 | A1 * | 7/2004 | Sugamoto | H01L 22/24 438/745 |
| 2013/0137277 | A1 * | 5/2013 | Huang | H01L 21/32134 438/753 |

FOREIGN PATENT DOCUMENTS

| JP | 07-263429 A | 10/1995 |
| JP | 07263429 | * 10/1995 |
| JP | 3651440 B2 | 5/2005 |

* cited by examiner

*Primary Examiner* — Kimberly Rizkallah
*Assistant Examiner* — Bo Bin Jang
(74) *Attorney, Agent, or Firm* — Foley & Lardner LLP (57) ABSTRACT

An etching method for detecting crystal defects, the method includes providing a substrate with an etchant containing hydrogen fluoride, nitric acid, hydrogen chloride, and water. A concave portion on a part having a crystal defect of the substrate is formed by the etchant. The concave portion is examined by a microscope to locate a position of the crystal defect.

17 Claims, 6 Drawing Sheets

FIG. 1A

- HF
- HNO₃
- CH₃COOH
- H₂O

FIG. 1B

- HF
- HNO₃
- HCl
- H₂O

|  | VOLUME COMPOSITION RATIO [ml] | | | |
| --- | --- | --- | --- | --- |
|  | HF(50.0%) | HNO$_3$ (69.5%) | HCl(35.5%) | H$_2$O |
| CONDITION 1 | 1 | 10-13 | 1-3 | 11-15 |
| CONDITION 2 | 1 | 10-13 | 4-6 | 11-15 |
| CONDITION 3 | 1 | 10-13 | 1-3 | 5-10 |
| CONDITION 4 | 1 | 10-13 | 4-6 | 5-10 |
| CONDITION 5 | 2 | 10-13 | 1-3 | 5-10 |
| CONDITION 6 | 2 | 10-13 | 4-6 | 5-10 |
| CONDITION 7 | 2 | 6-9 | 1-3 | 5-10 |
| CONDITION 8 | 2 | 6-9 | 4-6 | 5-10 |

*FIG. 2A*

|  | WEIGHT COMPOSITION RATIO [wt%] | | | |
| --- | --- | --- | --- | --- |
|  | HF | HNO$_3$ | HCl | H$_2$O |
| CONDITION 1 | 1.6-2.0 | 29.0-40.2 | 1.2-4.2 | 56.6-65.7 |
| CONDITION 2 | 1.5-1.7 | 26.2-36.2 | 4.3-7.5 | 57.4-65.5 |
| CONDITION 3 | 1.9-2.4 | 34.0-49.6 | 1.4-5.3 | 46.5-59.6 |
| CONDITION 4 | 1.7-2.1 | 30.3-43.6 | 4.9-9.2 | 48.7-60.1 |
| CONDITION 5 | 3.6-4.7 | 32.7-47.5 | 1.3-5.0 | 46.6-59.2 |
| CONDITION 6 | 3.3-4.1 | 29.3-42.0 | 4.7-8.8 | 48.7-59.8 |
| CONDITION 7 | 4.4-6.0 | 24.2-41.6 | 1.6-6.5 | 50.9-66.0 |
| CONDITION 8 | 3.9-5.1 | 21.1-35.7 | 5.6-11.0 | 52.9-65.8 |

| | WEIGHT COMPOSITION RATIO [wt%] | | | | PIT SIZE (μm) | ΔVALUE | PATTERN LENGTH (μm) |
|---|---|---|---|---|---|---|---|
| | HF | HNO₃ | HCl | H₂O | | | |
| CONDITION 1 | 1.6–2.0 | 29.0–40.2 | 1.2–4.2 | 56.6–65.7 | 0.03 | 25 | 0.31 |
| CONDITION 2 | 1.5–1.7 | 26.2–36.2 | 4.3–7.5 | 57.4–65.5 | 0.04 | 25 | 0.33 |
| CONDITION 3 | 1.9–2.4 | 34.0–49.6 | 1.4–5.3 | 46.5–59.6 | 0.17 | 33 | 0.21 |
| CONDITION 4 | 1.7–2.1 | 30.3–43.6 | 4.9–9.2 | 48.7–60.1 | 0.20 | 35 | 0.21 |
| CONDITION 5 | 3.6–4.7 | 32.7–47.5 | 1.3–5.0 | 46.6–59.2 | 0.42 | 50 | 0.15 |
| CONDITION 6 | 3.3–4.1 | 29.3–42.0 | 4.7–8.8 | 48.7–59.8 | 0.44 | 54 | 0.15 |
| CONDITION 7 | 4.4–6.0 | 24.2–41.6 | 1.6–6.5 | 50.9–66.0 | 0.83 | 67 | 0.11 |
| CONDITION 8 | 3.9–5.1 | 21.1–35.7 | 5.6–11.0 | 52.9–65.8 | 0.88 | 68 | 0.16 |
| Wright | | | | | 0.15 | 33 | 0.21 |

FIG. 7

|  | VOLUME COMPOSITION RATIO [ml] | | | | |
|---|---|---|---|---|---|
|  | HF (49–50%) | HNO$_3$ (69–71%) | CH$_3$COOH (99–100%) | H$_2$O | ADDITIVE |
| JIS–A | 1 | 12.7 | 3 | 3.7 |  |
| JIS–B | 1 | 12.7 | 3 | 5.7 |  |
| JIS–C | 1 | 12.7 | 1 | 6.7 |  |
| JIS–D | 2 | 12.7 | 2 | 6.7 |  |
| JIS–E | 1 | 2.5 | – | 10.5 | AgNO$_3$:0.005mol/L |
| JIS–F | 3 | 5.1 | – | 7.9 |  |
| JIS–G | 1 | 12.7 | – | 6.3 |  |
| JIS–H | 2 | 5.9 | 2 | 6.1 | KI:0.1–0.5g/L |
| JIS–I | 2 | 6.8 | 2 | 6.2 | KI:0.1–0.5g/L |

FIG. 8

|  | ETCHING LIQUID | TREATMENT TIME (SECONDS) | PIT SIZE (μm) | ΔVALUE |
|---|---|---|---|---|
| 1 | EMBODIMENT | 30 | 0.17 | 33 |
| 2 | Wright | 7 | 0.15 | 33 |
| 3 | JIS–B | 10 | 0.18 | 80 |
| 4 | JIS–C | 10 | 0.14 | 73 |
| 5 | JIS–D | 7 | 0.27 | 86 |
| 5 | JIS–D | 10 | 0.55 | 63 |
| 6 | JIS–G | 10 | 0.23 | 92 |

ETCHING METHOD AND ETCHANT

CROSS-REFERENCE TO RELATED APPLICATION

This application claims the benefit of and priority to Japanese Patent Application No. 2015-232057; filed Nov. 27, 2015, the entire contents of which are incorporated herein by reference.

FIELD

Embodiments described herein relate generally to an etching method.

BACKGROUND

When a crystal defect of a substrate is evaluated, an etching method is frequently used. In an etching method, a crystal defect is manifested as an etch pit by an etchant, and the etch pit is observed by an optical microscope or an electron microscope. When the substrate is a silicon substrate, examples of the etchant include a Sirtl etchant, a Secco etchant, and a Wright etchant. These etchants include hexavalent chromium which adversely affects the environment.

Therefore, the use of a chromeless etchant not containing chromium is reviewed. For example, in the Japanese Industrial Standards, a chromeless etchant containing hydrogen fluoride, nitric acid, acetic acid, and water is standardized as JIS H 0609. However, in this chromeless etchant, there is a problem in that selectivity in which a crystal defect is etched is low, or the etchant reacts with the substrate to generate a new crystal defect.

SUMMARY

In some embodiments according to one aspect, an etching method for detecting crystal defects may include providing a substrate with an etchant containing hydrogen fluoride, nitric acid, hydrogen chloride, and water. A concave portion on a part of the substrate having a crystal defect of the substrate may be formed by the etchant.

In some embodiments according to another aspect, an etchant for detecting crystal defects of a substrate may include hydrogen fluoride, nitric acid, hydrogen chloride, and water. Weight composition ratios of hydrogen fluoride, nitric acid, hydrogen chloride, and water in the etchant may be (1.7 to 2.4):(30.3 to 49.6):(1.4 to 9.2):(46.5 to 60.1), respectively.

Other aspects and embodiments of the disclosure are also encompassed. The foregoing summary and the following detailed description are not meant to restrict the disclosure to any particular embodiment but are merely meant to describe some embodiments of the disclosure.

DETAILED DESCRIPTION

An etching method in which a substrate can be appropriately treated by an etchant that is less detrimental to the environment is provided.

According to some embodiments, the etching method includes providing or treating the substrate with an etchant containing hydrogen fluoride, nitric acid, hydrogen chloride, and water. The method further includes forming a concave portion on a part of the substrate having a crystal defect by the etchant. The method further includes examining the concave portion.

Hereinafter, the example embodiments will be described with reference to the drawings.

Figure 1A:
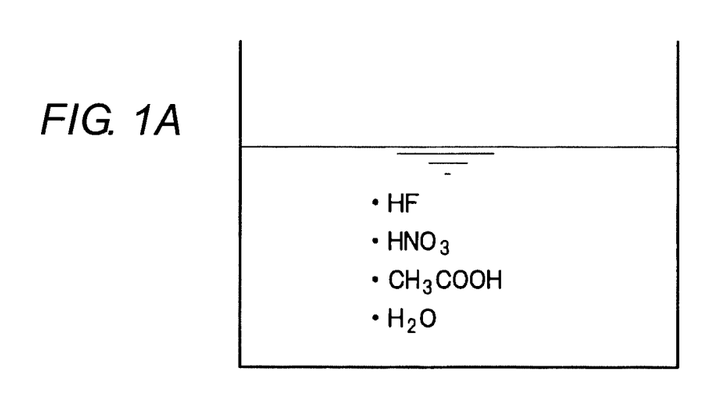
FIG. 1A and FIG. 1B are schematic views for describing a component of an etchant according to some embodiments.
Figure 1B:
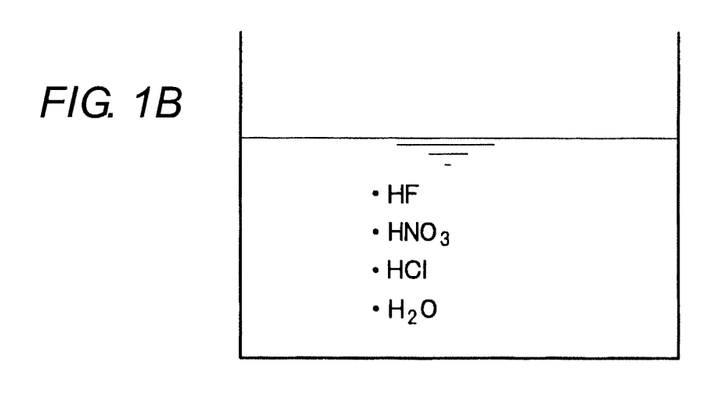

FIG. 1A and FIG. 1B are schematic views for describing a component of an etchant according to some embodiments.

FIG. 1A schematically illustrates a component of an etchant of Comparative Example. The etchant contains hydrogen fluoride (HF), nitric acid ($HNO_3$), acetic acid ($CH_3COOH$), and water ($H_2O$), but does not contain chromium such as hexavalent chromium in principle. An example of this etchant is a chromeless etchant standardized as JIS H 0609. In this etchant, at least some of HF molecules, HN03 molecules, and $CH_3COOH$ molecules are ionized.

FIG. 1B schematically illustrates a component of the etchant according to some embodiments. The etchant contains hydrogen fluoride (HF), nitric acid ($HNO_3$), hydrogen chloride (HCl), and water ($H_2O$), but does not contain chromium such as hexavalent chromium or an organic acid such as an acetic acid in principle. In this etchant, at least some of HF molecules, $HNO_3$ molecules, and HCl molecules are ionized.

In some embodiments of the present disclosure, the term "principle" is used as explained in the following. For example, when a certain etchant contains chromium as an impurity, this etchant corresponds to an "etchant not containing chromium in principle". Also, when chromium is intentionally contained in a certain etchant at a concentration that can contribute to etching, this etchant does not correspond to the "etchant not containing chromium in principle." Also, when a certain etchant allows chromium to be contained at a concentration that can contribute to etching, this etchant does not correspond to the "etchant not containing chromium in principle". For example, an etchant "not containing chromium in principle" may be substantially devoid of chromium such that a weight composition ratio of chromium to $H_2O$ in the etchant is less than 1:500, such as less than 1:1,000 or less than 1:5,000 or less than 1:10,000. The above applies to an organic acid in the same manner. For example, an etchant "not containing an organic acid in principle" may be substantially devoid of an organic acid such that a weight composition ratio of the organic acid to $H_2O$ in the etchant is less than 1:500, such as less than 1:1,000 or less than 1:5,000 or less than 1:10,000.

In some embodiments, the etchant illustrated in FIG. 1B is used instead of the etchant illustrated in FIG. 1A. That is, in some embodiments, a chromeless etchant containing hydrogen chloride instead of acetic acid is used.

Figure 2A:
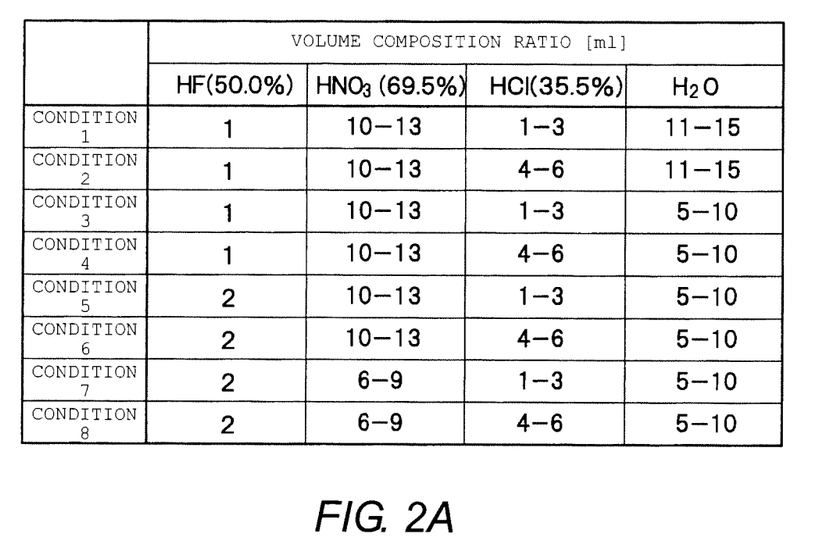
FIG. 2A and FIG. 2B are tables for describing a component of the etchant according to some embodiments.
Figure 2B:
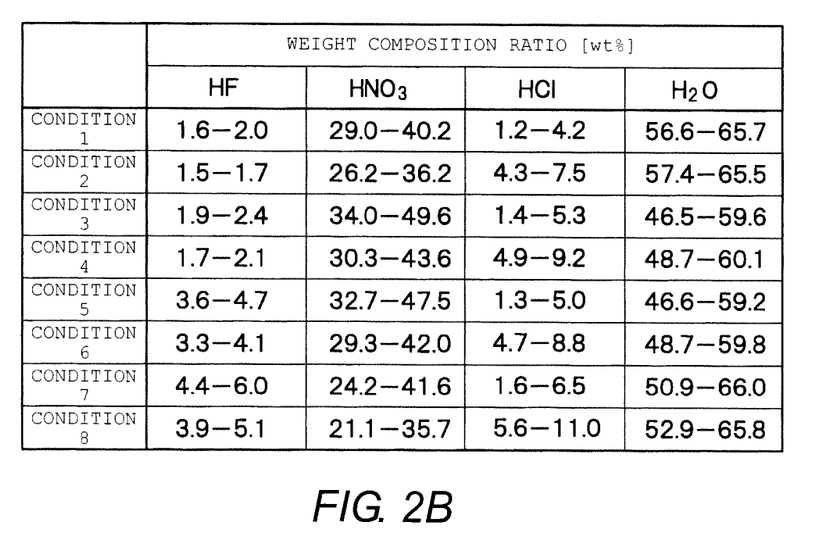

FIG. 2A and FIG. 2B are tables for describing a component of the etchant according to some embodiments.

FIG. 2A illustrates eight types of the etchants produced by mixing a HF aqueous solution (hydrofluoric acid) having a concentration of 50.0%, a $HNO_3$ aqueous solution having a concentration of 69.5%, a HCl aqueous solution (hydrochloric acid) having a concentration of 35.5%, and pure water. These etchants correspond to a specific example of the etchant illustrated in FIG. 1B.

These etchants are prepared by mixing the HF aqueous solution, the $HNO_3$ aqueous solution, the HCl aqueous solution, and the pure water at various volume (e.g., milliliter or mL) composition ratios. For example, an etchant of condition 1 is produced by mixing the HF aqueous solution, the $HNO_3$ aqueous solution, the HCl aqueous solution, and the pure water at a volume composition ratio of 1:(10 to 13):(1 to 3):(11 to 15).

The etchants of conditions 1 to 8 in FIG. 2B are respectively the same as the etchants of conditions 1 to 8 in FIG. 2B. However, in FIG. 2B, the volume composition ratio in FIG. 2A is converted into a weight (e.g., gram or g) composition ratio. For example, in condition 1, the weight composition ratios of HF, $HNO_3$, HCl, and $H_2O$ in the etchant are (1.9 to 2.4): (34.0 to 49.6): (1.4 to 5.3): (46.5 to 59.6), respectively.

In addition, when the volume composition ratio is converted into the weight composition ratio, molecular weights of HF, $HNO_3$, HCl, and $H_2O$ are set to 20.01 g/mol, 63.00 g/mol, 36.46 g/mol, and 18.02 g/mol, respectively. In addition, densities of the HF aqueous solution, the $HNO_3$ aqueous solution, the HCl aqueous solution, and pure water are set to 1.16 g/ml, 1.41 g/ml, 1.18 g/ml, and 0.998 g/ml (density at a temperature of 20° C.).

FIG. 3A, FIG. 3B, FIG. 3C and FIG. 3D are cross-sectional views illustrating a crystal defect evaluation method according to some embodiments.

Figure 3A:
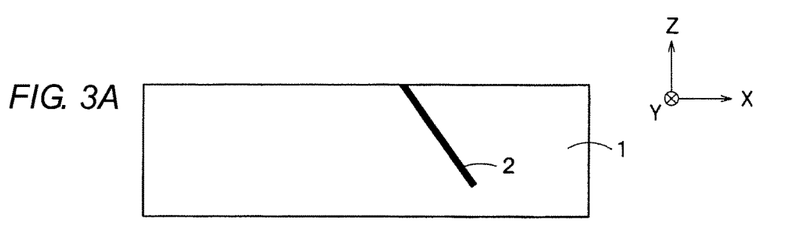
FIG. 3A, FIG. 3B, FIG. 3C and FIG. 3D are cross-sectional views illustrating a crystal defect evaluation method according to some embodiments.

FIG. 3A illustrates a substrate 1 of an examination target. An example of the substrate 1 is a semiconductor wafer such as a silicon wafer. The substrate 1 illustrated in 3A has a crystal defect 2. An example of the crystal defect 2 is a dislocation or a slip.

FIG. 3A specifies that an X direction and a Y direction are parallel to the surface of the substrate 1 and perpendicular to each other, and illustrates an XZ plane where it is specified that a z direction is perpendicular to the surface of the substrate 1. In some embodiments of the present disclosure, a +Z direction is treated as an upper direction and a −Z direction is treated as a lower direction. The −Z direction according to some embodiments may or may not coincide with a gravitational direction.

In some embodiments, after various layers configuring a device structure are formed on the substrate 1, these layers are removed from the substrate 1 (this separation is referred to as "pre-treatment"). These layers are separated by, for example, dipping the substrate 1 into hydrofluoric acid. FIG. 3A illustrates the substrate 1 after these layers are separated.

Figure 3B:
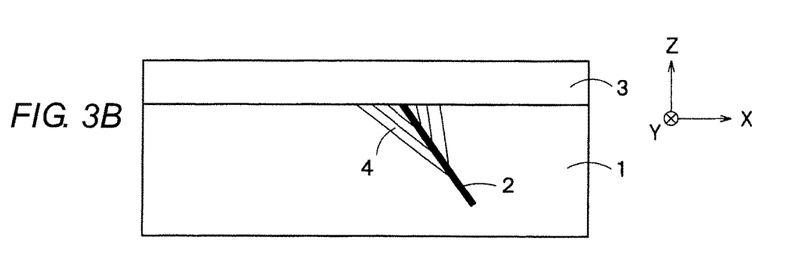

Next, in some embodiments, the substrate 1 is cleaved and the substrate 1 is dipped into a selected etchant 3 (see FIG. 3B). The selected etchant 3 according to some embodiments is, for example, an etchant that, according to any one of conditions 1 to 8 mentioned above, contains hydrogen fluoride, nitric acid, hydrogen chloride, and water. In some embodiments, the substrate 1 may be dipped into the selected etchant 3 without being cleaved.

In some embodiments, if the selected etchant 3 is provided to the substrate 1, the surface of the substrate 1 may be oxidized by an oxidizing agent in the selected etchant 3, and an oxide film may be formed on the surface of the substrate 1. For example, nitric acid or the like functions as an oxidizing agent of silicon and a silicon oxide film is formed on the surface of the substrate 1. This oxide film is quickly etched by hydrogen fluoride or the like, which functions as an etching agent in the selected etchant 3.

Figure 3C:
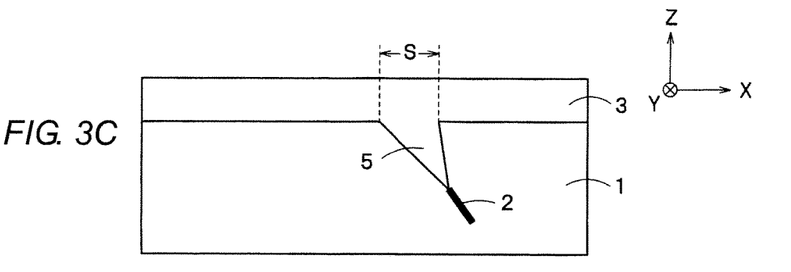

At this time, an oxidization rate of a part having the crystal defect 2 is faster than an oxidization rate of the other parts, which are, for example, a perfect crystal. As a result, the part having the crystal defect 2 is considerably etched by the selected etchant 3. FIG. 3B illustrates a state where an oxide film 4 is formed on the part having the crystal defect 2 by the selected etchant 3. FIG. 3C illustrates a state where the oxide film 4 is removed by the selected etchant 3. In FIG. 3C, an oxide film 4 on the part having the crystal defect 2 is etched and a concave portion referred to as an etch pit 5 is formed on this part. A symbol S indicates a size (e.g., a length) of the etch pit 5.

In some embodiments, the etch pit 5 may be formed by oxidization illustrated in FIG. 3B and etching illustrated in FIG. 3C. However, the etch pit 5 may be formed on the part of having the crystal defect 2 by another mechanism. For example, the oxide film 4 is not formed but the etch pit 5 is formed.

Figure 3D:
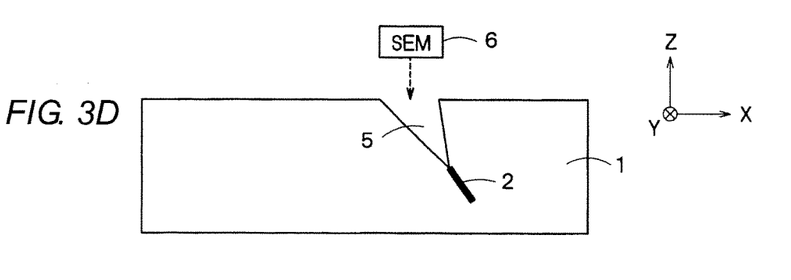

Next, in some embodiments, the etch pit 5 is observed by an optical microscope or an electron microscope to examine the etch pit 5 (see FIG. 3D). For example, by measuring the position or distribution of the etch pit 5, the position, distribution, shape, or the like of the crystal defect 2 can be specified and the reason of the crystal defect 2 can be analyzed. In FIG. 3D, the etch pit 5 is observed by a SEM (Scanning Electron Microscope).

Figure 4:
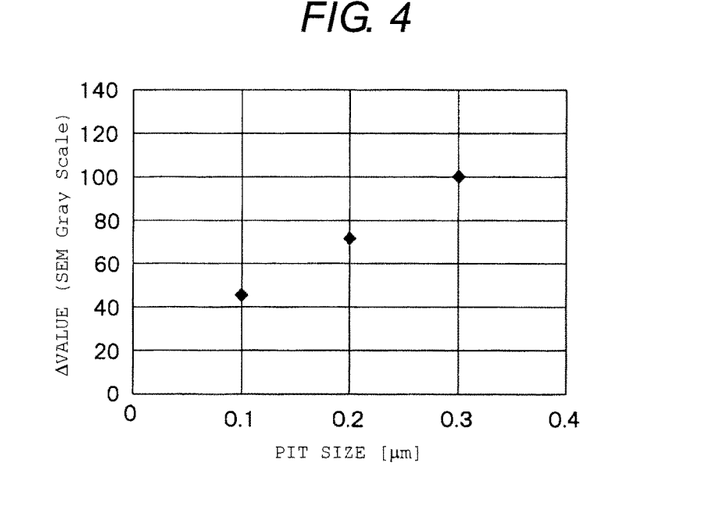
FIG. 4 is a graph for describing Δvalue of a scanning electron microscope (SEM) image.
Figure 5:
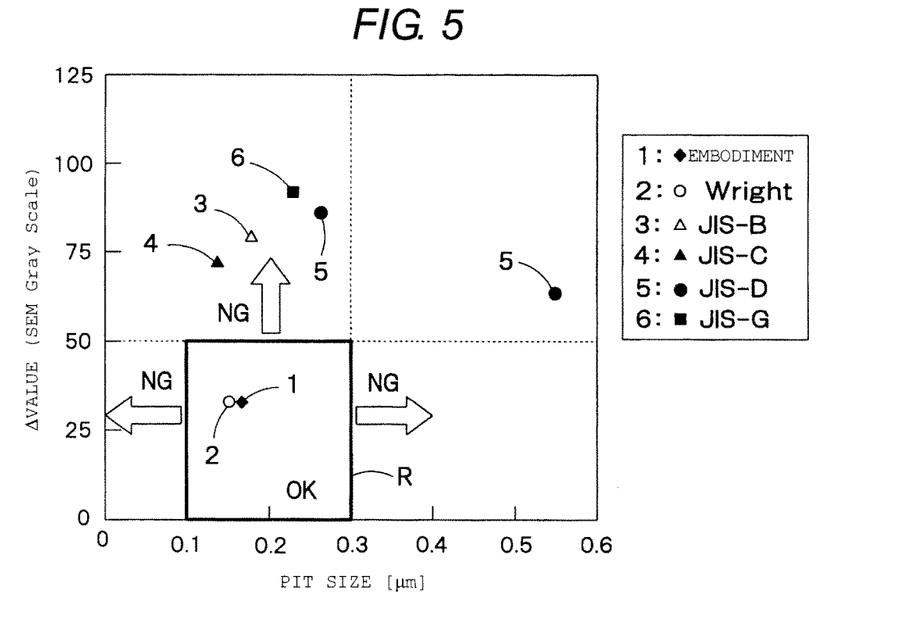
FIG. 5 is a graph for describing performance of the etchant according to some embodiments.
Figure 6:
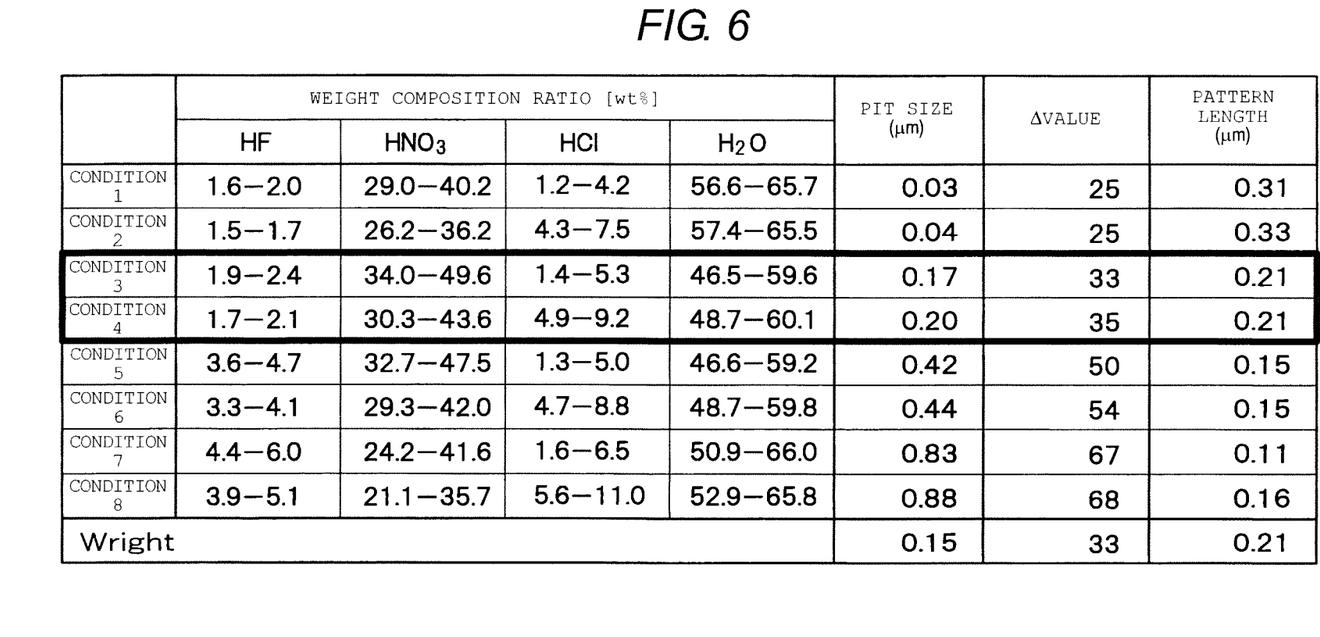
FIG. 6 is a table for describing performance of the etchant according to some embodiments.

Next, performance of the etchant according to some embodiments will be described with reference to FIG. 4, FIG. 5 and FIG. 6. FIG. 4, FIG. 5 and FIG. 6 illustrate an experimental result obtained by executing the steps of FIG. 3A, FIG. 3B, FIG. 3C and FIG. 3D using various etchants and observing the substrate 1 in FIG. 3D by the SEM 6.

FIG. 4 is a graph for describing Δvalue of a SEM image.

A horizontal axis of FIG. 4 indicates a size (pit size) of the etch pit 5. A vertical axis of FIG. 4 indicates a Δvalue of a SEM image obtained by observing the substrate 1 by the SEM 6. In some embodiments, the Δvalue is calculated by indicating each pixel of the SEM image with a gray scale value of 0 to 255 white and black gradation, calculating a differential value between the gray scale value and a reference value of each pixel, and averaging the differential values over all pixels.

The Δvalue is assumed to represent roughness of the surface of the substrate 1 because as the surface of the substrate 1 is rougher, a variation of the gray scale value within the SEM image becomes greater. In some embodiments (as shown in FIG. 4), the Δvalue is calculated from the SEM image in which a bottom surface of an element separation region (or shallow trench isolation (STI)) of the substrate 1 is observed. Accordingly, the Δvalue of FIG. 4 can represent roughness of the bottom surface of the element separation region.

In general, it is considered that if the etch pit 5 is formed on the substrate 1, the surface of the substrate 1 becomes rough. In addition, it is considered that as the size of the etch pit 5 becomes larger, the roughness of the surface of the substrate 1 becomes greater. Meanwhile, FIG. 4 illustrates that the pit size and the Δvalue have a positive correlation. That is, FIG. 4 illustrates that as the size of the etch pit 5 is larger, the Δvalue becomes greater. The above indicates that the assumption that the Δvalue represents roughness of the surface of the substrate 1 is reasonable.

FIG. 5 is a graph for describing performance of the etchant according to some embodiments.

Figure 7:
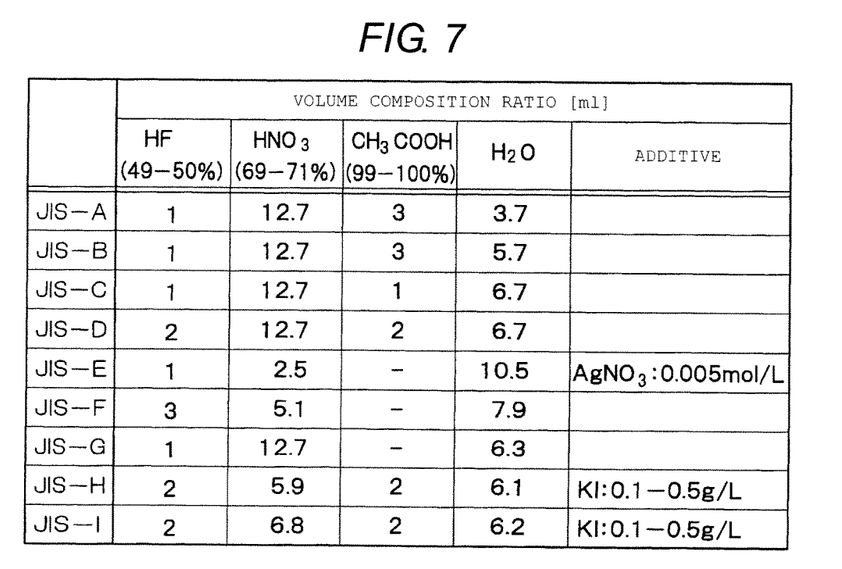
FIG. 7 is a table illustrating a component of an etchant of Comparative Example.

FIG. 5 illustrates a measurement result of the pit size and the Δvalue when the etchant (1), the Wright etchant (2), the JIS-B liquid (3), the JIS-C liquid (4), the JIS-D liquid (5), and the JIS-G liquid (6) according to some embodiments are used. These JIS liquids are chromeless etchants standardized as JIS H 0609, and correspond to the etchant of Comparative Example illustrated in FIG. 1A. Refer to FIG. 7 with regard to the details of a component of the JIS liquids (e.g., JIS-A, JIS-B, JIS-C, JIS-D, JIS-E, JIS-F, JIS-G, JIS-H, and JIS-I. FIG. 7 is a table illustrating a component of an etchant of Comparative Example. In FIG. 7, the components of the JIS liquids are shown as a volume composition ratio.

Next, a region R illustrated in FIG. 5 will be described.

In general, the pit size becomes larger as the treatment time (e.g., etching time) of the substrate 1 by the selected etchant 3 is longer. However, if the pit size is too large, the size of the etch pit 5 with respect to the size of the crystal defect 2 becomes too large, and it may be difficult to specify a position having the crystal defect 2. Meanwhile, if the pit size is too small, it may be difficult to detect the etch pit 5 by the SEM 6. Therefore, the pit size according to some embodiments may be from 0.1 μm to 0.3 μm.

In some embodiments, the roughness of the surface of the substrate 1 is desirably less because if the roughness of the surface of the substrate 1 is greater, it may be difficult to distinguish the concave portion by the etch pit 5 and other concave portions. Therefore, the Δvalue according to some embodiments may be 50 or less.

Referring to FIG. 5, the region R indicates a range in which the pit size is 0.1 μm to 0.3 μm and the Δvalue is 50 or less. In some embodiments, the pit size and the Δvalue may take the values within the region R.

When the Wright etchant is used, the pit size and the Δvalue can take the values within the region R by appropriately setting the etching time. However, the Wright etchant contains hexavalent chromium which adversely affects the environment.

Meanwhile, since the JIS-B liquid, the JIS-C liquid, the JIS-D liquid, and the JIS-G liquid do not contain chromium in principle, the influence on the environment is small. However, when these JIS liquids are used, the pit size and the Δvalue are in a trade-off relationship and are difficult to be controlled to be within the region R.

Since the etchant according to some embodiments does not contain chromium in principle, the influence on the environment is small. In addition, when the etchant according to some embodiments is used, the pit size and the Δvalue can take the values within the region R by appropriately setting the etching time. Therefore, according to some embodiments, the substrate 1 can be appropriately treated by the etchant which less affects the environment, and both adjustment of the pit size and reduction of roughness of the surface can be obtained.

FIG. 6 is a table for describing performance of the etchant according to some embodiments.

FIG. 6 illustrates the pit size, the Δvalue, and a pattern length when the etchants of conditions 1 to 8 are used. The pattern length indicates a length of a predetermined device pattern on the substrate 1 which is measured after etching. In general, the pattern length becomes shorter as the etching time of the substrate 1 becomes longer. If the pattern length varies greatly, it may be difficult to specify the occurrence position of the crystal defect 2. Therefore, in some embodiments, the variation of the pattern length may be small.

FIG. 6 further illustrates the pit size, the Δvalue, and the pattern length when the Wright etchant is used. In FIG. 6, the pattern length is 0.21 μm when the Wright etchant is used. Therefore, the pattern length may be greater than 0.21 μm or the same as 0.21 μm, when the etchants of conditions 1 to 8 are used.

Hereinafter, a measurement result of the pit size, the Δvalue, and the pattern length will be described with reference to FIG. 6.

Condition 1

After the selected etchant 3 satisfying the condition 1 is prepared and the substrate 1 which is pretreated is dipped into the selected etchant 3, the substrate 1 is observed by the SEM 6. As a result, the pattern length is 0.31 μm, which is satisfactory. In addition, the Δvalue is 25, which is satisfactory. However, the pit size is 0.03 μm, which is smaller than a desired value (e.g., 0.1 to 0.3 μm).

Condition 2

After the selected etchant 3 satisfying the condition 2 is prepared and the substrate 1 which is pretreated is dipped into the selected etchant 3, the substrate 1 is observed by the SEM 6. As a result, the pattern length is 0.33 μm, which is satisfactory. In addition, the Δvalue is 25, which is satisfactory. However, the pit size is 0.04 μm, which is smaller than a desired value (e.g., 0.1 to 0.3 μm).

Condition 3

After the selected etchant 3 satisfying the condition 3 is prepared and the substrate 1 which is pretreated is dipped into the selected etchant 3, the substrate 1 is observed by the SEM 6. As a result, the pattern length is 0.21 μm, which is satisfactory. In addition, the Δvalue is 33, which is satisfactory. In addition, the pit size is 0.17 μm, which is satisfactory.

Condition 4

After the selected etchant 3 satisfying the condition 4 is prepared and the substrate 1 which is pretreated is dipped into the selected etchant 3, the substrate 1 is observed by the SEM 6. As a result, the pattern length is 0.21 μm, which is satisfactory. In addition, the Δvalue is 35, which is satisfactory. In addition, the pit size is 0.20 μm, which is satisfactory.

Condition 5

After the selected etchant 3 satisfying the condition 5 is prepared and the substrate 1 which is pretreated is dipped into the selected etchant 3, the substrate 1 is observed by the SEM 6. As a result, the pattern length, the Δvalue, and the pit size are respectively, 0.15 μM, 50, and 0.42 μm, all of which fall outside satisfactory ranges.

Condition 6

After the selected etchant 3 satisfying the condition 6 is prepared and the substrate 1 which is pretreated is dipped into the selected etchant 3, the substrate 1 is observed by the SEM 6. As a result, the pattern length, the Δvalue, and the pit size are respectively, 0.15 μm, 54, and 0.44 μm, all of which fall outside satisfactory ranges.

Condition 7

After the selected etchant 3 satisfying the condition 7 is prepared and the substrate 1 which is pretreated is dipped into the selected etchant 3, the substrate 1 is observed by the SEM 6. As a result, the pattern length, the Δvalue, and the pit size are respectively, 0.11 μm, 67, and 0.83 μm, all of which fall outside satisfactory ranges.

Condition 8

After the selected etchant 3 satisfying the condition 8 is prepared and the substrate 1 which is pretreated is dipped into the selected etchant 3, the substrate 1 is observed by the SEM 6. As a result, the pattern length, the Δvalue, and the pit size are respectively, 0.16 μm, 68, and 0.88 μm, all of which fall outside satisfactory ranges.

From the above result, in the crystal defect evaluation method according to some embodiments, the etchant of condition 3 or condition 4 may be used. That is, the weight composition ratios of HF, $HNO_3$, HCl, and $H_2O$ in the etchant according to some embodiments may be "1.9 to 2.4":"34.0 to 49.6":"1.4 to 5.3":"46.5 to 59.6", respectively or, "1.7 to 2.1":"30.3 to 43.6":"4.9 to 9.2": "48.7 to 60.1", respectively.

Accordingly, if the conditions 3 and 4 are summarized, the weight composition ratios of HF, $HNO_3$, HCl, and $H_2O$ in the etchant according to some embodiments may be (1.7 to 2.4):(30.3 to 49.6):(1.4 to 9.2):(46.5 to 60.1), respectively. In this case, the etchant according to some embodiments has at least the same performance as that of the Wright etchant, even though the liquid does not contain chromium in principle.

In the etchant containing HF, $HNO_3$, HCl, and $H_2O$, if the amount of HCl is relatively small (e.g., when the weight composition ratio of HCl to $H_2O$ is less than 1.4:60.1), it is considered that the etchant actions may be similar to the JIS liquids and may cause the surface of the substrate 1 to be considerably rough. Meanwhile, if the amount of HCl is relatively large (e.g., when the weight composition ratio of HCl to $H_2O$ is larger than 9.2:46.5), it is considered that the etchant may etch the oxide film 4 (e.g., a silicon oxide film) but may also etch the substrate 1 (e.g., a silicon substrate) considerably so as to cause the etch pit 5 to be difficult to discern. According to some embodiments, by setting the weight composition ratios of HF, $HNO_3$, HCl, and $H_2O$ in the etchant to (1.7 to 2.4):(30.3 to 49.6):(1.4 to 9.2):(46.5 to 60.1), respectively, the etchant with at least the same performance as that of the Wright etchant can be realized.

As the above, the etchant according to some embodiments contains HF, $HNO_3$, HCl, and $H_2O$. Therefore, according to some embodiments, the substrate 1 can be appropriately treated by the etchant which less affects the environment.

In addition, the etchant according to some embodiments may contain other substances in addition to HF, $HNO_3$, HCl, and $H_2O$. For example, the etchant according to some embodiments may contain a substance for increasing performance of the etchant or a substance not deteriorating the performance of the etchant excessively. Even when the etchant according to some embodiments contains such a substance, the pit size and the Δvalue may take the values within the region R of FIG. 5. The same applies to additional embodiments as described below.

Figure 8:
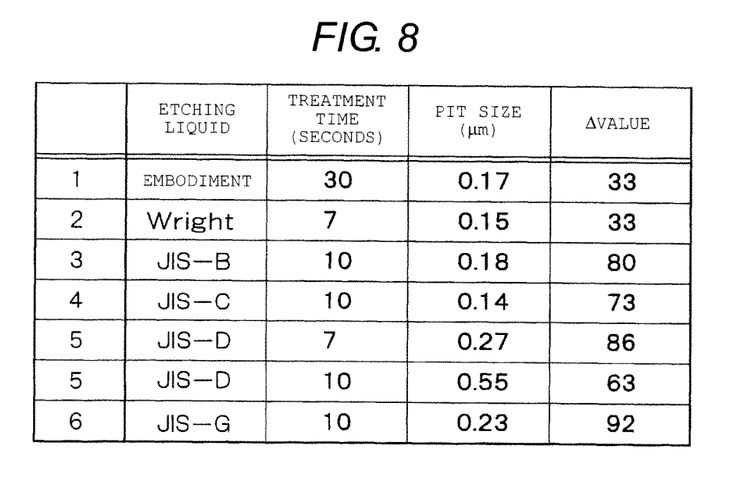
FIG. 8 is a table for describing a crystal defect evaluation method according to some embodiments.

FIG. 8 is a table for describing a crystal defect evaluation method according to some embodiments.

FIG. 8, in the same manner as FIG. 5, illustrates a measurement result of the pit size and the Δvalue when the etchant, the Wright etchant, the JIS-B liquid, the JIS-C liquid, the JIS-D liquid, and the JIS-G liquid according to some embodiments are used. The numbers "1 to 6" illustrated in FIG. 8 correspond to the numbers "1 to 6" illustrated in FIG. 5. The etchant according to some embodiments is the etchant of condition 3.

In some embodiments, when the substrate 1 is manually treated by the selected etchant 3, the treatment time of the substrate 1 by the selected etchant 3 may be about 10 seconds to 10 minutes. If the treatment time is shorter than 10 seconds, a several-seconds error of the manual operation greatly affects an examination result, while if the treatment time is longer than 10 minutes, efficiency of the manual operation is low.

When the Wright etchant is used, the pit size and the Δvalue take the values within the region R by setting the treatment time to 7 seconds (see FIG. 8). However, since the treatment time is shorter than 10 seconds, an error of the manual operation greatly affects the examination result. For example, due to the error of the manual operation, the pit size and the Δvalue may not take the values within the region R.

FIG. 8 illustrates an example in which the treatment time is set to 7 seconds when the JIS-D liquid is used, and an example in which the treatment time is set to 10 seconds when the JIS-D liquid is used. These examples show that the pit size and the Δvalue are greatly changed over 3 seconds.

Meanwhile, when the etchant according to the embodiments as shown in FIG. 1, FIG. 2 and FIG. 3 is used, the pit size and the Δvalue take the values within the region R by setting the treatment time to 30 seconds (see the first row in the table of FIG. 8). Accordingly, in some embodiments, an error of the manual examination operation less affects the examination result. Therefore, the etchant according to some embodiments has an advantage such as excellent etching controllability and ease in treatment during examination compared to the Wright etchant or the JIS liquids.

While certain embodiments have been described, these embodiments have been presented by way of example only, and are not intended to limit the scope of the present disclosure. Indeed, the embodiments described herein may be embodied in a variety of other forms; furthermore, various omissions, substitutions and changes in the form of the embodiments described herein may be made without departing from the spirit of the present disclosure. The accompanying claims and their equivalents are intended to cover such forms or modifications as would fall within the scope and spirit of the present disclosure. Moreover, some or all of the above described embodiments can be combined when implemented.

What is claimed is:

1. An etching method for detecting crystal defects, the method comprising:
   providing a substrate with an etchant comprising hydrogen fluoride, nitric acid, hydrogen chloride, and water, the substrate having a crystal defect; and
   forming a concave portion on the crystal defect by the etchant,
   wherein weight composition ratios of hydrogen fluoride, nitric acid, hydrogen chloride, and water in the etchant are (1.7 to 2.4):(30.3 to 49.6):(1.4 to 9.2):(46.5 to 60.1), respectively, and
   wherein the etchant does not contain chromium or acetic acid in principle.

2. The method according to claim 1, further comprising:
   using a microscope, locating a position of the crystal defect according to the concave portion.

3. The method according to claim 1,
   wherein the size of the concave portion is 0.1 μm to 0.3 μm.

4. The method according to claim 1, further comprising:
   forming a film on the part of the substrate having the crystal defect by the etchant; and
   removing the film by the etchant to form the concave portion on the substrate.

5. The method according to claim 4,
   wherein the film is formed by oxidization of the substrate.

6. The method according to claim 1,
wherein a treatment time of the substrate by the etchant is 10 seconds to 10 minutes.

7. The method according to claim 1,
wherein the etchant does not contain an organic acid in principle.

8. The method according to claim 1, wherein a weight composition ratio of chromium to $H_2O$ in the etchant is less than 1:500.

9. The method according to claim 1, wherein at least one of hydrogen fluoride, nitric acid, hydrogen chloride in the etchant includes ionized molecules.

10. An etching method for detecting crystal defects, the method comprising:
providing a substrate with an etchant comprising an oxidizing agent, an etching agent, hydrogen chloride, and water, the substrate having a crystal defect; and
forming a concave portion on the crystal defect by the etchant,
wherein weight composition ratios of hydrogen fluoride, nitric acid, hydrogen chloride, and water in the etchant are (1.7 to 2.4):(30.3 to 49.6):(1.4 to 9.2):(46.5 to 60.1), respectively, and
wherein the etchant does not contain chromium or acetic acid in principle.

11. The method according to claim 10, further comprising:
using a microscope, locating a position of the crystal defect according to the concave portion.

12. The method according to claim 10, wherein the oxidizing agent is nitric acid, and the etching agent is hydrogen fluoride.

13. The method according to claim 10,
wherein the size of the concave portion is 0.1 μm to 0.3 μm.

14. The method according to claim 10,
wherein a treatment time of the substrate by the etchant is 10 seconds to 10 minutes.

15. The method according to claim 10,
wherein the etchant does not contain an organic acid in principle.

16. The method according to claim 10, wherein a weight composition ratio of chromium to $H_2O$ in the etchant is less than 1:500.

17. The method according to claim 10, wherein at least one of hydrogen fluoride, nitric acid, hydrogen chloride in the etchant includes ionized molecules.

* * * * *